United States Patent
Fujimoto

(10) Patent No.: US 8,507,286 B1
(45) Date of Patent: Aug. 13, 2013

(54) METHOD OF ANALYZING OXIDATION STATE OF METHIONINE IN PROTEIN SAMPLE

(75) Inventor: Hirotaka Fujimoto, Kashiwa (JP)

(73) Assignee: Shimadzu Corporation, Kyoto (JP)

( * ) Notice: Subject to any disclaimer, the term of this patent is extended or adjusted under 35 U.S.C. 154(b) by 782 days.

(21) Appl. No.: 12/274,928

(22) Filed: Nov. 20, 2008

(30) Foreign Application Priority Data

Nov. 26, 2007 (JP) ................ 2007-304789

(51) Int. Cl.
*G01N 33/00* (2006.01)

(52) U.S. Cl.
USPC ............ 436/86; 424/9.34; 435/106; 435/131; 436/89; 436/542; 530/300; 530/302

(58) Field of Classification Search
None
See application file for complete search history.

(56) References Cited

U.S. PATENT DOCUMENTS

2008/0299542 A1* 12/2008 Loscalzo ............ 435/4

OTHER PUBLICATIONS

Conesa et al., Journal of Biological Chemistry, "Expression of the *Caldariomyces fumago* chloroperoxidase in *Aspergillus niger* and characterization of the recombinant enzyme", vol. 10 (Feb. 2001).*
Harry Schachter, et al, "Preferential Oxidation of the Methionine Residue Near the Active Site of Chymotrypsin", The Journal of Biological Chemistry, Mar. 1964, p. 813-829, vol. 239, No. 3.

* cited by examiner

*Primary Examiner* — Dirk Bass
(74) *Attorney, Agent, or Firm* — Sughrue Mion, PLLC

(57) ABSTRACT

Disclosed is a method of analyzing an oxidation state of a methionine residue in a protein sample, which comprises the steps of: inducing a reaction between a protein sample having a methionine residue with an oxidation state to be analyzed, and hydrogen peroxide $H_2{}^{18}O_2$ having oxygen atoms labeled by the isotope $^{18}O$, to obtain a modified protein sample in which the oxidation state of the methionine residue is stabilized; and subjecting the modified protein sample to a measurement to quantify an oxidation degree of the methionine residue. Preferably, the measurement is a mass spectrometric (MS) measurement using a mass spectrometer. The method can analyze an oxidation state of a methionine residue in a protein sample, in a simple manner, while accurately reflecting an in vivo oxidation state of the methionine residue.

4 Claims, 4 Drawing Sheets

Present Invention

Accurate measurement reflecting in vivo oxidation state

Conventional Method

Inaccurate measurement failing to reflect in vivo oxidation state

- ～ : Non-oxidized methionine residue-containing peptide
- ～○ : $^{16}O$-oxidized methionine residue-containing peptide
- ～○* : $^{18}O$-oxidized methionine residue-containing peptide

METHOD OF ANALYZING OXIDATION STATE OF METHIONINE IN PROTEIN SAMPLE

BACKGROUND OF THE INVENTION

1. Field of the Invention

The present invention belongs to the fields of protein chemistry, peptide chemistry, mass analysis and diagnostic medicine, and relates to a method of analyzing an oxidation state of a methionine residue in a protein sample.

2. Description of the Related Art

Heretofore, as a quantification method for an oxidized methionine residue, there have been employed various methods, such as a method based on alkaline hydrolysis of a protein sample, a method based on alkylation and hydrolysis of a methionine residue, and a method based on bromocyan cleavage and acid hydrolysis. In these conventional methods, methionine sulfoxide after hydrolyzation is detected and quantified by measuring UV absorption spectra using a liquid chromatography (LC) system. A method based on alkylation using iodoacetate labeled by the radioisotope carbon-14 ($^{14}C$), and hydrolysis, has also been employed (see, for example, SCHACHTER H; DIXON GH, "Preferential oxidation of the methionine residue near the active site of chymotrypsin", Journal of Biological Chemistry, March 1964, Vol. 239, pp 813-829). In this method, methionine sulfoxide after hydrolyzation is detected and quantified by radioactivity measurement.

It is reported that protein oxidation occurring in vivo causes decrease in protein activity and development of toxicity, and is deeply involved in diseases, such as cataract, lung emphysema, rheumatism, asthma, and metabolic syndrome and cardiovascular diseases including arteriosclerosis, and further in Alzheimer's disease and aging. The protein oxidation does not occur equally at any in vivo site but there are an oxidation-susceptible site and an oxidation-insusceptible site. It would have a significant meaning for a clarification of vital phenomena and structure-activity relationships to know a site and degree of protein oxidation under in vivo or in-vitro conditions.

The present invention focuses on an oxidation degree of a methionine residue. A methionine residue is an amino-acid residue susceptible to oxidation, and therefore receives great attention in researches on oxystress and aging-related changes.

However, the conventional methods are incapable of accurately quantifying an oxidized methionine residue.

For example, the above quantification methods using ultraviolet-visible spectra cannot quantify an oxidized methionine residue with acceptable accuracy. Moreover, the conventional methods are designed to determine an oxidation rate for the entire protein, and thereby it is unable to find out at what site of a protein and to what degree a methionine residue is oxidized.

As shown in FIG. 1B, in the conventional methods, a methionine residue which has not been oxidized in vivo is likely to be accidentally oxidized in a pretreatment stage to be performed in advance of a measurement operation, due to its oxidation-susceptible property. Consequently, the measurement is liable to fail to accurately reflect the in vivo oxidation state. That is, there is a problem of credibility of a measurement result.

For example, an oxidation-state measuring method may comprise preparing a target sample with an oxidation state to be measured, and a reference sample to be compared with the target sample, subjecting the two samples to a pretreatment, and comparing between respective measurement results of the two pretreated samples (i.e., two-group comparison analysis).

In this method, if a certain difference is detected in the two-group comparison analysis, it will be assumed that there is a difference between respective oxidation states of the two samples. However, such a difference is likely to be detected in the following situations involving accidental oxidation in the pretreatment stage: one situation where, when there is no difference between respective in vivo oxidation states of the two samples, accidental oxidation occurs mostly in one of the samples in the pretreatment stage, and a resulting difference is detected; and another situation where, when there is a certain difference between respective in vivo oxidation states of the two samples, accidental oxidation occurs mostly in one of the samples in the pretreatment stage, and a resulting difference changed from the difference between the in vivo oxidation states is detected.

Further, even if no difference is detected in the two-group comparison analysis, the detection result representing no difference is likely to come out in the following situation involving accidental oxidation in the pretreatment stage: a situation where, when there is a certain difference between respective in vivo oxidation states of the two samples, accidental oxidation occurs mostly in one of the samples in the pretreatment stage, and respective oxidation states of the samples incidentally become identical to each other after completion of the pretreatment.

In either situation, there is a possibility of failing to accurately maintain an in vivo oxidation state. Moreover, the above method requires preparing both a target sample and a reference sample, which leads to a problem about increase in analysis time and cost.

SUMMARY OF THE INVENTION

In view of the above circumstances, it is an object of the present invention to provide a method capable of analyzing an oxidation state of a methionine residue in a protein sample, in a simple manner, while accurately reflecting an in vivo oxidation state of the methionine residue.

Through various researches, the inventor found that the object of the present invention can be achieved by subjecting a protein sample to a previously-unimplemented treatment for stabilizing an in vivo oxidation state of a methionine residue in a protein sample to keep the in vivo oxidation state of the methionine residue until an oxidation-state measurement. Based on this knowledge, the present invention has been accomplished.

Specifically, the present invention has the following features.

(1) A method of analyzing an oxidation state of a methionine residue in a protein sample, which comprises the steps of: inducing a reaction between a protein sample having a methionine residue with an oxidation state to be analyzed, and hydrogen peroxide $H_2{}^{18}O_2$ having oxygen atoms labeled by the isotope $^{18}O$, to obtain a modified protein sample in which the oxidation state of the methionine residue is stabilized; and subjecting the modified protein sample to a measurement to quantify an oxidation degree of the methionine residue In this specification, the term "protein" is used as a meaning including a peptide having a relatively small molecular mass.

Further, the term "analyzing an oxidation state" is used as a meaning including "quantifying an oxidation degree" or "quantifying an oxidation degree and determining (or specifying) an oxidized site".

In the present invention, means for the measurement is a type capable of quantitatively distinguishing between a naturally-oxidized methionine residue possibly existing in a specific environment, such as a living body, and an artificially-oxidized methionine residue modified by an oxidation treatment using the hydrogen peroxide $H_2^{18}O_2$.

Given that a protein having an originally oxidized methionine residue is a $^{16}O$-oxide, and a protein having a methionine residue oxidized by $H_2^{18}O_2$ (which corresponds to an originally non-oxidized methionine residue) is a $^{18}O$-oxide, respective oxidation states of the two samples can be determined based on a fact that an intensity obtained by subtracting an intensity of a signal of a secondary isotope of the $^{16}O$-oxide (i.e., an isotope of the $^{16}O$-oxide having a mass number greater than that of a principal isotope of the $^{16}O$-oxide by 2), from a total intensity of a signal of the principal isotope and the signal of the secondary isotope, is equivalent to an intensity of a signal of a principal isotope of the $^{18}O$-oxide (which corresponds to the protein having the originally non-oxidized methionine residue).

(2) Preferably, in the method set forth in (1), the measurement is a mass spectrometric (MS) measurement using a mass spectrometer.

In the measurement using a mass spectrometer, the oxidation states can be determined based on a fact that an intensity obtained by subtracting a peak intensity of a secondary isotope ion of the $^{16}O$-oxide (i.e., an isotope ion of the $^{16}O$-oxide having a mass number greater than that of a principal ion of the $^{16}O$-oxide by 2), from an intensity at overlapping between a peak of the principal ion and a peak of the secondary isotope ion, is equivalent to a peak intensity of a principal ion of the $^{18}O$-oxide (which corresponds to the protein having the originally non-oxidized methionine residue).

(3) Preferably, the method set forth in (2) further comprises the step of subjecting the modified protein sample to an $MS^n$ measurement (wherein n is an integer of 2 or more) to specify an oxidized site of the methionine residue.

The method set forth in (3) is one example of a method of determining an oxidized site of a methionine residue in a protein sample.

(4) A method of analyzing an oxidation state of a methionine residue in a protein sample, which comprises: a step (i) of inducing a reaction between a first protein sample A having a methionine residue with an oxidation state to be analyzed, and hydrogen peroxide $H_2^{18}O_2$ having oxygen atoms labeled by the isotope $^{18}O$, to obtain a first modified protein sample A' in which the oxidation state of the methionine residue is stabilized, and subjecting the first modified protein sample A' to a measurement to quantify an oxidation degree of the methionine residue in the first modified protein sample A'; a step (ii) of inducing a reaction between a second protein sample B having a methionine residue with an oxidation state to be analyzed, and hydrogen peroxide $H_2^{18}O_2$ having oxygen atoms labeled by the isotope $^{18}O$, to obtain a second modified protein sample B' in which the oxidation state of the methionine residue is stabilized, and subjecting the second modified protein sample B' to a measurement to quantify an oxidation degree of the methionine residue in the second modified protein sample B'; and a step (iii) of comparing between respective measurement results in the step (i) and the step (ii).

The method set forth in (4) is one example of inter-group comparison analysis based on the method set forth in (1).

Thus, in the method set forth in (4), the measurement may be a mass spectrometric (MS) measurement using a mass spectrometer. Further, the method set forth in (4) may further comprise the step of subjecting the modified protein sample to an $MS^n$ measurement (wherein n is an integer of 2 or more) to specify an oxidized site of the methionine residue. Based on the method set forth in (4), two-group comparison analysis or three or more-group comparison analysis can be performed.

The present invention can provide a method capable of analyzing an oxidation state of a methionine residue in a protein sample while accurately reflecting an in vivo oxidation state of the methionine residue.

Specifically, the method of the present invention provides the following functions and advantages.

(1) An in vivo oxidation state of a methionine residue in a protein sample can be "stabilized".

(2) An in vivo oxidation state of a methionine residue in a protein sample can be accurately quantified.

(3) An oxidized site of a methionine residue in a protein sample can be specified, for example, through an $MS^n$ measurement (wherein n is an integer of 2 or more), to determine at what site of the protein and to what degree the methionine residue is oxidized.

(4) The method designed to perform two-group comparison analysis can be applied to a medical field. For example, based on comparison between a sample of diseased protein and a sample of healthy protein, the method can be used for diagnosis of diseases and prognostic prediction about medical procedure in the field of clinical medicine, and for detection of pathologic markers. Further, inter-group comparison analysis can be performed for various other types of samples.

DESCRIPTION OF THE PREFERRED EMBODIMENTS

Figure 1A:
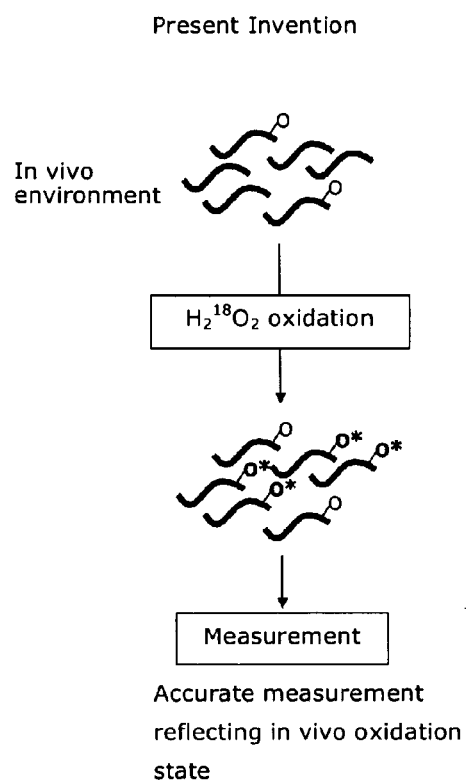
FIG. 1 is a schematic diagram showing a method of the present invention and a conventional method in a comparative manner to explain that an in vivo oxidation state in the method of the present invention is stabilized until a measurement operation, whereas an in vivo oxidation state in the conventional method can be changed before the measurement operation.
Figure 1B:
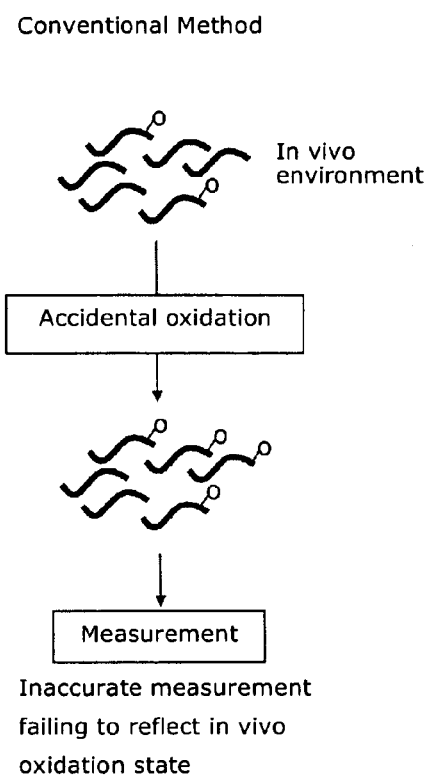

[Stabilization of Oxidation State of Methionine Residue]

In the present invention, the term "stabilizing an oxidation state of a methionine residue" means that when a protein (including a peptide) placed in a specific environment is placed in a second environment other than the specific environment, an oxidation state of a methionine residue in the protein is maintained without a change between an oxidation degree of the methionine residue in the protein placed in the specific environment and an oxidation degree of the methionine residue in the protein placed in the second environment.

The present invention is particularly useful when the specific environment is an in vivo environment. For example, in an in vivo environment, a methionine residue-containing peptide can exist as a mixture of an oxide (i.e., a portion of the peptide having an oxidized methionine residue, methionine sulfoxide) and a non-oxide (i.e., a portion of the peptide having a non-oxidized methionine residue). When a specific vital phenomenon arises from an in vivo existence rate of the oxide (i.e., in vivo oxidation degree), it is critical for a clarification of the vital phenomenon to accurately analyze an in vivo oxidation state of the methionine residue. The method of the present invention is particularly useful when a protein sample having a methionine residue with an oxidation state to be stabilized is, but not limited to, a protein sample collected from a living body.

In the present invention, the second environment other than the specific environment means any environment to which a protein which has existed in the specific environment is exposed until the protein is subjected to a measurement. For example, the second environment includes an environment of pretreatment, such as a desalting treatment, a solubilization treatment, a drying treatment, a re-solubilization treatment, a reductive alkylation treatment, a fragmentation treatment, a fractionation treatment, a concentration treatment or a heating treatment. In any environment where oxygen exists, a possibility of occurrence of accidental oxidation cannot be denied.

In an operation of stabilizing an oxidation state of a plurality of methionine residues in a protein sample, ones of the methionine residues, which are not oxidized in the specific environment, are artificially modified in the following manner. That is, in the stabilizing operation, the non-oxidized methionine residues are modified into a form capable of being distinguished from naturally-oxidized methionine residues possibly existing in the specific environment, by means for measuring the protein sample.

For example, the stabilizing operation may include an oxidation treatment for artificially creating oxidized methionine residues which have the same structure as that of naturally-oxidized methionine residues (i.e., methionine residues naturally oxidized in vivo), except a mass number of oxygen. The artificially-oxidized methionine residues and the naturally-oxidized methionine residues can be distinguished from each other by mass spectrometry.

Preferably, an oxidant for the oxidation treatment is a type having the $^{18}O$ isotope of oxygen and being capable of substantially fully oxidizing only non-oxidized methionine residues. Specifically, hydrogen peroxide ($H_2^{18}O_2$) labeled by the isotope $^{18}O$ is used.

As shown in FIG. 1A, for example, when a peptide sample collected from a living body is subjected to an oxidation treatment using hydrogen peroxide $H_2^{18}O_2$ ($H_2^{18}O_2$ oxidation), all methionine residues which have not been oxidized in vivo are oxidized by $^{18}O$, so that the entire peptide sample is protected from any further oxidation until it is subjected to a measurement operation. That is, an in vivo oxidation state (i.e., an oxidation state of a $^{16}O$-oxide) is maintained until the measurement operation, without the risk of undergoing accidental oxidation before the measurement operation as in the conventional methods. This makes it possible to perform the measurement operation while accurately reflecting the in vivo oxidation state.

The hydrogen peroxide $H_2^{18}O_2$ may be used in the form of an aqueous solution. In this case, a concentration of the hydrogen peroxide $H_2^{18}O_2$ varies depending on a type of protein sample and other conditions, and is therefore not limited to a specific value. For example, an aqueous solution containing 0.1 to 10 mM hydrogen peroxide $H_2^{18}O_2$ may be used. More specifically, an aqueous solution containing 10 mM hydrogen peroxide $H_2^{18}O_2$ may be used.

For example, in the aqueous solution containing 10 mM hydrogen peroxide $H_2^{18}O_2$, the hydrogen peroxide $H_2^{18}O_2$ may be contained in an amount of 1 to 100 μL with respect to 200 pmol of protein sample.

Conditions of an oxidation reaction using the hydrogen peroxide $H_2^{18}O_2$ are not particularly limited. For example, a reaction temperature may be set in the range of zero to 100 degrees, and a reaction time may be in the range of 15 minutes to 100 hours or may be set at greater than 100 hours.

When a protein sample is subjected to the oxidation treatment for the stabilizing operation, there is a possibility that an amino-acid residue theoretically undergoing oxidation (e.g., tryptophan residue) exists in protein molecules. However, as long as the oxidation reaction using the hydrogen peroxide $H_2^{18}O_2$ is performed under the above condition, only the non-oxidized methionine residues can be oxidized while preventing the remaining amino-acid residues from undergoing oxidation.

[Pretreatment for Measurement]

The protein sample subjected to the oxidation treatment for the oxidation-state stabilizing operation may be appropriately subjected to an additional pretreatment for measurement. The protein sample having the methionine residues with the stabilized oxidation state is allowed to be subjected to a wide variety of treatments. For example, the protein sample may be subjected to one or more treatments selected from the group consisting of a desalting treatment, a solubilization treatment, a drying treatment, a re-solubilization treatment, a reductive alkylation treatment, a fragmentation treatment, a fractionation treatment, a concentration treatment and a heating treatment.

A technique for performing each of the above pretreatments is not limited to a specific type, but may be appropriately determined in a manner which should be apparent to those skilled in the art.

For example, the desalting treatment may be performed using a commonly used desalting column, such as Sephadex® column. The solubilization treatment may be performed using a denaturant, such as urea, guanidinium hydrochloride, or surfactant including sodium dodecyl sulfate (SDS). A concentration of the denaturant is not limited to a specific value, but may be appropriately determined to allow the protein sample to be solubilized and denaturalized, in consideration of a type of protein sample and other conditions and in a manner which should be apparent to those skilled in the art. The re-solubilization treatment may be performed in the same manner as that in the solubilization treatment. The reductive alkylation treatment may be performed in a conventional manner. The fragmentation treatment may be performed based on digestion using an enzyme, such as trypsin, or chemical fragmentation. The fractionation treatment may be performed based, for example, on a technique using a high-performance liquid chromatography (HPLC) system including a reverse-phase column. A technique for performing the concentration treatment may include an immunoprecipitation technique.

[Measurement of Sample with Stabilized Oxidation State]

The protein sample subjected to the oxidation treatment and then appropriately subjected the additional pretreatment is subjected to the measurement operation. The measurement means may be a type capable of quantitatively distinguishing between the naturally-oxidized methionine residues possibly existing in the specific environment and the artificially-oxidized methionine residues modified by the oxidation treatment. Further, means for specifying a site of a $^{16}O$-oxide may be combined with the measurement means to determine at what site of the protein and to what degree a methionine residue is oxidized.

In the present invention, a mass spectrometer is preferably used as the measurement means. The mass spectrometer may be a matrix-assisted laser desorption/ionization (MALDI) type. In this case, an MALDI-TOF (Time-Of-Flight) mass spectrometer (e.g., AXIMA®-CFR plus produced by Shimadzu Co./Kratos Analytical Ltd.) or an MALDI-QIT (Quadrupole Ion Trap)-TOF mass spectrometer (e.g., AXIMA®-QIT produced by Shimadzu Co./Kratos Analytical Ltd.) may be used.

In case of the MALDI mass spectrometer, a matrix is not limited to a specific type. For example, the matrix may be DHBA (2,5-dihydrooxybenzoic acid), or 4-CHCA (α-cyano-4-hydroxycinnamic acid)

The oxidation state can be quantitatively determined from a specific peak intensity in mass spectra obtained by the mass spectrometric (MS) measurement. Details of MS spectrum analysis will be described later in connection with the following Example.

Further, an MS/MS measurement or MS$^n$ measurement (n: integer of 3 or more) may be performed using a tandem mass spectrometer to specify at what site of the protein a methionine residue is oxidized.

[Inter-Group Comparison Analysis]

In inter-group comparison analysis to be performed based on the method of the present invention, two or more samples to be compared with each other are not particularly limited, but a wide variety of samples may be used in a manner which should be apparent to those skilled in the art. For example, the samples may include samples for detection of pathologic markers, and samples for diagnosis of diseases and prognostic prediction about medical procedure. When such samples are used, the method of the present invention may be implemented as follows. Firstly, a sample of diseased protein (protein sample A) and a sample of healthy protein (protein sample B) are prepared. Then, for each of the two samples, the operation of stabilizing an oxidation state of a methionine residue, and the additional pretreatment, are performed, and the modified protein sample having the methionine residue with the stabilized oxidation state is subjected to the measurement, in the aforementioned manner. Then, respective measurement results on the two samples are compared with each other.

EXAMPLES

The present invention will be more specifically described based on an example where the method of the present invention employs mass spectrometry, and uses a peptide preparation (Neurokinin A). A sequence of Neurokinin A is HKTDS-FVGLM-NH$_2$ (SEQ ID NO: 1). In this sequence, M-NH$_2$ shows that a C-terminal methionine residue is amidated. Neurokinin A has one methionine residue, and this methionine residue will undergo oxidation by an oxidation treatment.

Example 1

A Neurokinin A sample [1-0] having a non-oxidized methionine residue, and a Neurokinin A sample [2-0] having a partially-oxidized methionine residue, were prepared. Specifically, the sample [1-0] was prepared by incubating 100 pmol of Neurokinin A in 10 mL of water at a constant temperature of 4° C. for 2 days. The sample [2-0] was prepared by incubating 100 pmol of Neurokinin A, in 10 mL of water containing hydrogen peroxide ($H_2^{16}O_2$) in a concentration of 1 mM, at a constant temperature of 4° C. for 2 days.

Figure 2:
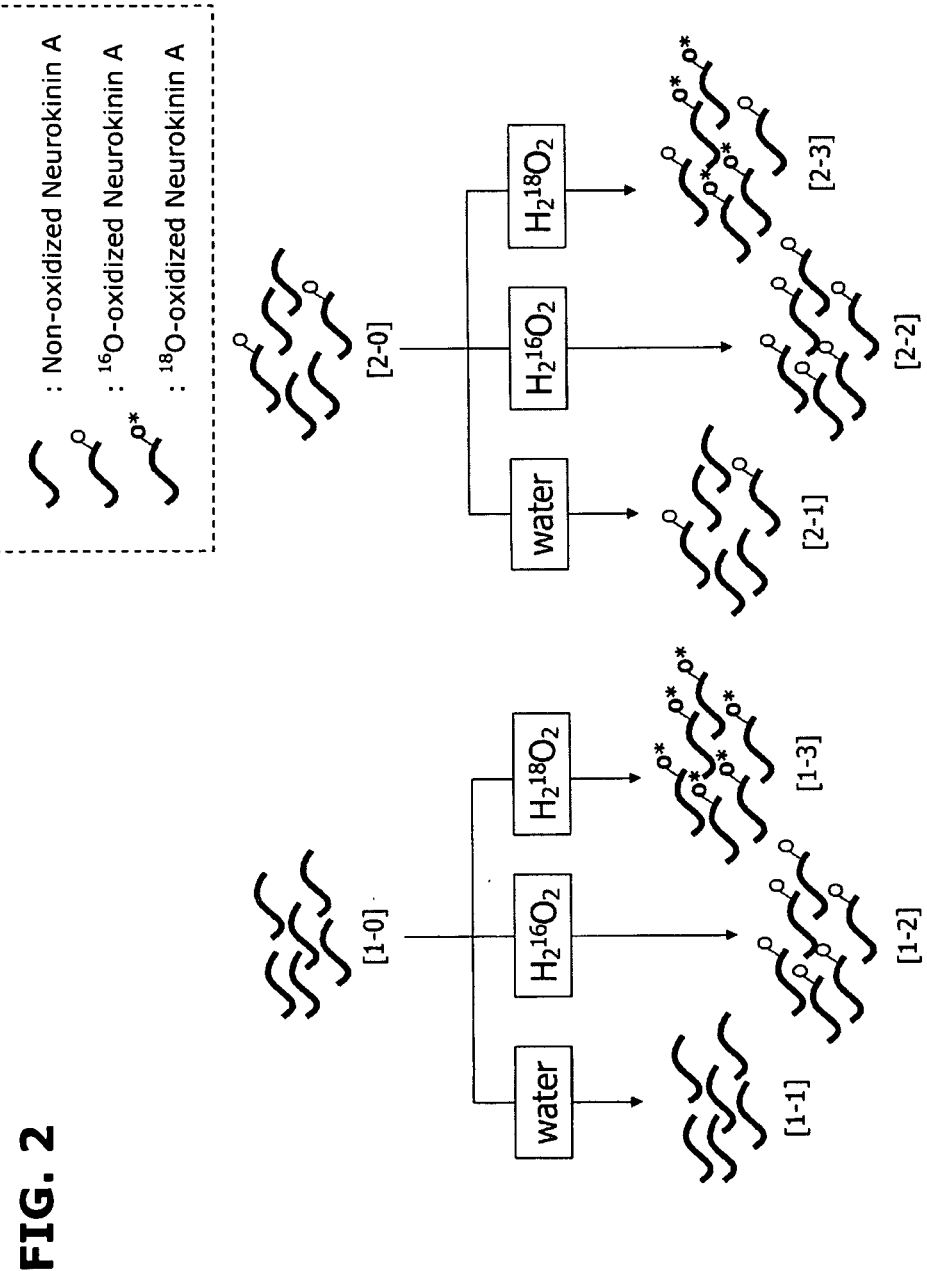
FIG. 2 is a schematic diagram showing an operation of preparing a sample in Example 1.

As shown in FIG. 2, each of the sample [1-0] and the sample [2-0] was subjected to the following three types of treatments A to C to obtain six samples [1-1], [1-2], [1-3], [2-1], [2-2], [2-3].

<A. Incubation in Water (for Comparison)>

30 pmol of the Neurokinin A sample was dissolved in 10 μL of water, and incubated at 4° C. for 100 hours.

<B. Oxidation Using $H_2^{16}O_2$ (for Comparison)>

30 pmol of the Neurokinin A sample was dissolved in 10 μL of water containing hydrogen peroxide ($H_2^{16}O_2$) in a concentration of 10 mM, and incubated at 4° C. for 100 hours. Through an oxidation reaction, the non-oxidized methionine residue was fully oxidized by $^{16}O$.

<C. Oxidation Using $H_2^{18}O_2$>

30 pmol of the Neurokinin A sample was dissolved in 10 μL of water containing hydrogen peroxide ($H_2^{18}O_2$) in a concentration of 10 mM, and incubated at 4° C. for 100 hours. Through an oxidation reaction, the non-oxidized methionine residue was fully oxidized by $^{18}O$.

Each of the samples [1-0], [1-1], [1-2], [1-3], [2-0], [2-1], [2-2], [2-3] was subjected to mass spectrometry. In the mass spectrometry, 2,5-dihydroxy benzoic acid was used as a matrix, and AXIMA®-CFR plus (produced by Shimadzu Co./Kratos Analytical Ltd.) was used as a mass spectrometer to perform the measurement in reflectron mode.

Figure 3:
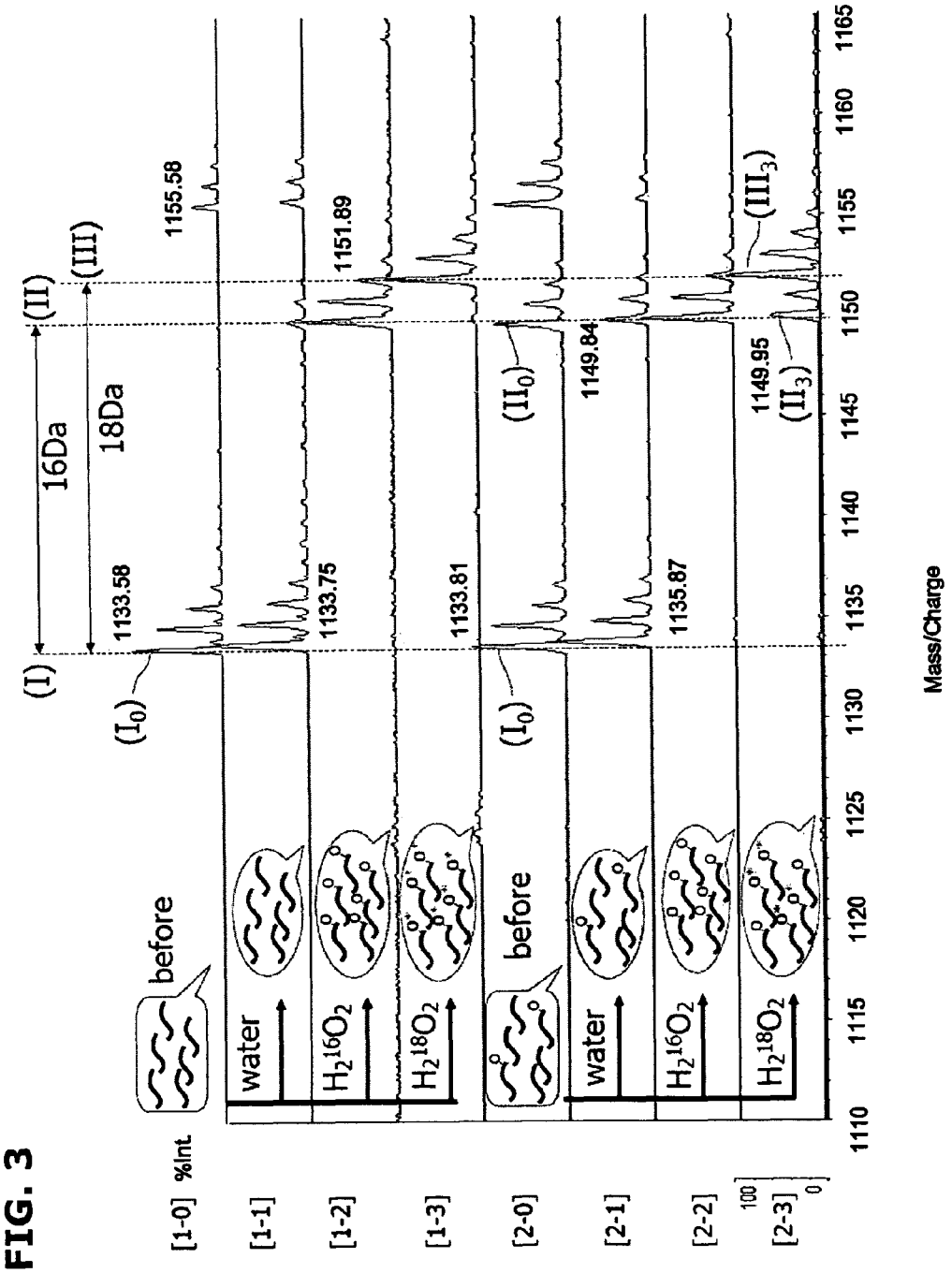
FIG. 3 is a chart showing mass spectra obtained in Example 1.

FIG. 3 shows obtained mass spectra.

As for the Neurokinin A sample [1-0] having an originally non-oxidized methionine residue, a peak of methionine residue-containing Neurokinin A (i.e., non-oxidized methionine residue-containing Neurokinin A: hereinafter referred to simply as "non-oxide") was detected at the position (I). A principal ion peak of this non-oxide is expressed as (Io).

As for the sample [1-1] subjected to no oxidation treatment, the peak of the non-oxide was also detected at the position (I).

As for the sample [1-2] subjected the $H_2^{16}O_2$ oxidation treatment, the peak (Io) of the Neurokinin A in the spectrum of the sample [1-0] subjected to no oxidation treatment disappeared, and a peak of $^{16}O$-oxidized Neurokinin A (hereinafter referred to simply as "$^{16}O$-oxide") was detected at the position (II) having a mass-to-charge ratio (m/z) greater than that at the peak (Io) by 16 Da. From this result, it was verified that the methionine residue of the Neurokinin A is substantially fully oxidized by $^{16}O$ through the $H_2^{16}O_2$ oxidation treatment.

Similarly, as for the sample [1-3] subjected the $H_2^{18}O_2$ oxidation treatment, the peak (Io) of the Neurokinin A in the spectrum of the sample [1-0] subjected to no oxidation treatment disappeared, and a peak of $^{18}O$-oxidized Neurokinin A (hereinafter referred to simply as "O-oxide") was detected at the position (III) having a mass-to-charge ratio (m/z) greater than that at the peak (Io) by 18 Da. From this result, it was verified that the methionine residue of the Neurokinin A is substantially fully oxidized by $^{18}O$ through the $H_2^{18}O_2$ oxidation treatment.

As for the Neurokinin A sample [2-0] having an originally partially-oxidized methionine residue, a peak of the non-oxide was detected at the position (I), and a peak of the oxide was detected at the position (II) having a mass-to-charge ratio (m/z) greater than that at the position (I) by 16 Da was detected. A principal ion peak of this non-oxide is expressed as (Io), and a principal ion peak of this oxide is expressed as (IIo).

As for the sample [2-1] subjected to no oxidation treatment, two peaks similar to those in the sample [2-0] were obtained.

As for the sample [2-2] subjected the $H_2{}^{16}O_2$ oxidation treatment, the peak (Io) of the non-oxide in the spectrum of the sample [2-0] disappeared, and only a peak of the $^{16}$O-oxide was detected. From this result, it was verified that the non-oxidized methionine residue of the Neurokinin A is substantially fully oxidized by $^{16}$O through the $H_2{}^{16}O_2$ oxidation treatment.

As for the sample [2-3] subjected the $H_2{}^{18}O_2$ oxidation treatment, the peak (Io) of the non-oxide disappeared, and a peak of the $^{18}$O-oxide was detected at the position (III) having a mass-to-charge ratio (m/z) greater than that at the peak (Io) by 18 Da. A principal ion peak of this $^{18}$O-oxide is expressed as (III$_3$). Further, a peak identical to the peak (IIo) of the $^{16}$O-oxide in the spectrum of the sample [2-0] was detected. The peak of this $^{16}$O-oxide is expressed as (II$_3$).

In the spectrum of the sample [2-3], a different between respective mass-to-charge ratios at the peak (II$_3$) of the $^{16}$O-oxide and the peak (III$_3$) of the $^{18}$O-oxide is 2 Da. Thus, the peak (III$_3$) of the $^{18}$O-oxide overlaps a part of isotopic peaks of the peak (II$_3$) of the $^{16}$O-oxide.

Figure 4A:
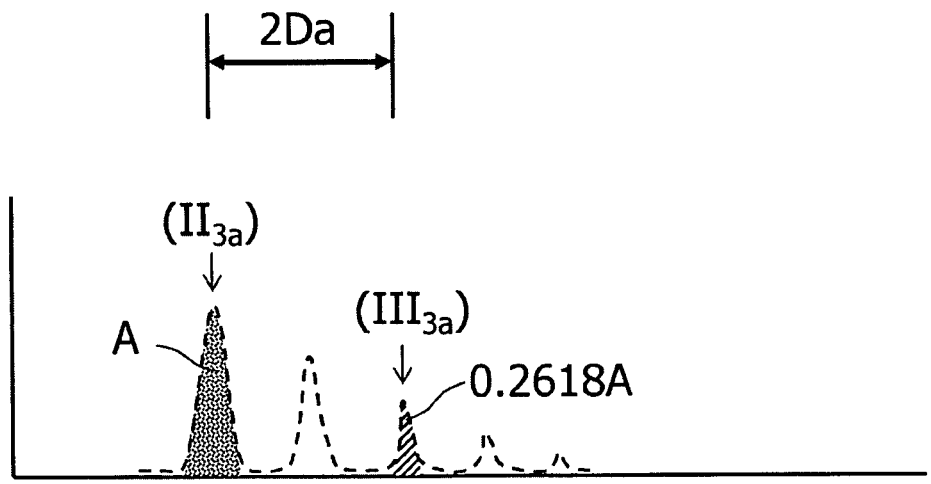
FIGS. 4A to 4C are graphs for explaining a process of calculating an oxidation degree of an original protein sample in Example 1.
Figure 4B:
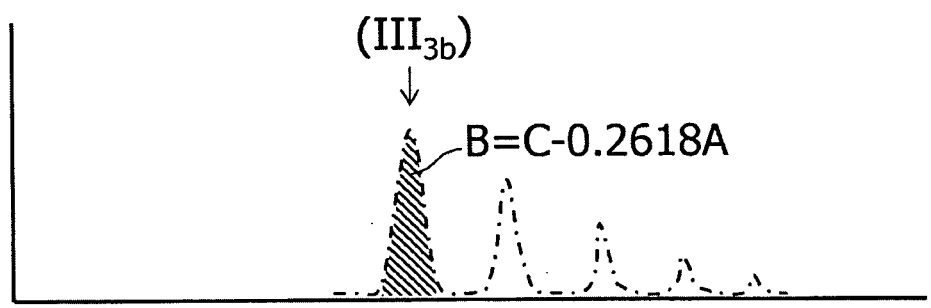
Figure 4C:
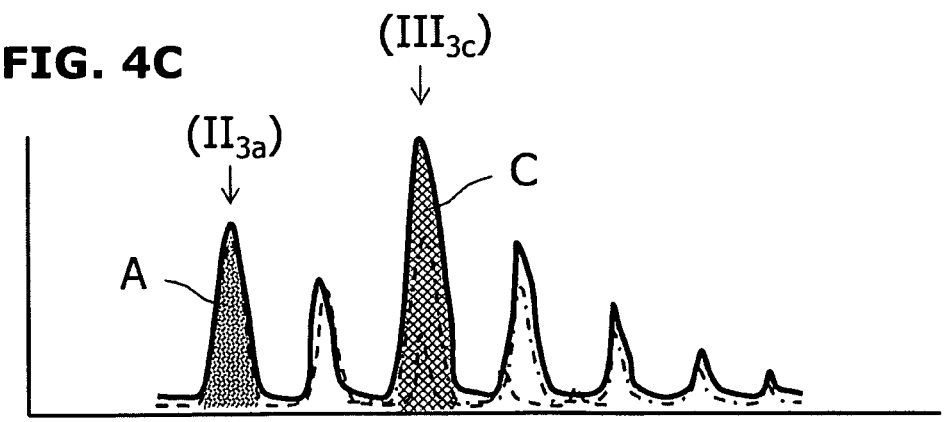

Thus, a region having this overlapping between the peaks, i.e., a region having a mass-to-charge ratio of about 1148 to 1157 in the spectrum of the sample [2-3] in FIG. 3, is enlarged and shown in FIG. 4C. The solid line in FIG. 4C indicates peaks actually obtained from the sample [2-3]. These peaks are formed by superimposing peaks indicated by the dotted line in FIG. 4A on peaks indicated by the one-dot chain line in FIG. 4B. That is, the peaks in FIG. 4A correspond to peaks of the $^{16}$O-oxide in the sample [2-3], and the peaks in FIG. 4B correspond to peaks of the $^{18}$O-oxide in the sample [2-3].

In FIG. 4A, a principal ion peak of the $^{16}$O-oxide is expressed as (II$_{3a}$), and a 2nd isotopic ion peak of the $^{16}$O-oxide, i.e., an isotopic ion peak having a mass-to-charge ratio greater that at the peak (II$_{3a}$) by 2 Da, is expressed as (III$_{3a}$). Further, in FIG. 4B, a principal ion peak of the $^{18}$O-oxide is expressed as (III$_{3b}$).

The principal ion peak (III$_{3b}$) of the $^{18}$O-oxide has the same mass-to-charge ratio (m/z) as that at the 2nd isotopic ion peak (III$_{3a}$) which inherently arises from the $^{16}$O-oxide. Thus, these two peaks overlap each other to form the peak (III$_{3c}$) as shown in FIG. 4C, and the peak (III$_{3c}$) is detected.

In order to analyze an oxidation state of the sample [2-0], it is necessary to determine a ratio between oxidized methionine residue-containing Neurokinin A and non-oxidized methionine residue-containing Neurokinin A in the sample [2-0] (i.e., an oxidation degree of the sample [2-0]). In the method of the present invention, an original oxidation state is stabilized. Thus, the signal (II$_3$) of the $^{16}$O-oxide in the sample [2-3] accurately reflects an oxidation state of the original sample [2-0]. That is, a ratio between oxidized methionine residue-containing Neurokinin A and non-oxidized methionine residue-containing Neurokinin A in the sample [2-0] is reflected as a ratio between the $^{16}$O-oxide and the $^{18}$O-oxide in the sample [2-3].

Therefore, given that an intensity of the principal ion peak (II$_{3a}$) of the $^{16}$O-oxide is A, and an intensity of the principal ion peak (III$_{3b}$) of the $^{18}$O-oxide is B, an oxidation state of the sample [2-0] can be analyzed by determining A and B.

In the spectrum of the sample [2-3], the principal ion peak (II$_{3a}$) of the $^{16}$O-oxide and the peak (III$_{3c}$) are detected. That is, the intensity B of the principal ion peak (III$_{3b}$) of the $^{18}$O-oxide is not directly detected. However, given that an intensity of the peak (III$_{3c}$) is C, the intensity B can be derived from the intensity A of the principal ion peak (II$_{3a}$) of the $^{16}$O-oxide and the intensity C of the peak (III$_{3c}$). Specifically, the peak (III$_{3c}$) is formed by superimposing the isotopic ion peak (III$_{3a}$) of the $^{16}$O-oxide and the principal ion peak (III$_{3b}$) of the $^{18}$O-oxide, and thereby a difference between the intensity C of the peak (III$_{3c}$) and the isotopic ion peak (III$_{3a}$) corresponds to the intensity B of the principal ion peak (III$_{3b}$) of the $^{18}$O-oxide.

An intensity of the isotopic ion peak (III$_{3a}$) of the $^{16}$O-oxide is appropriately derived based on an existence rate of isotopes of atoms making up the Neurokinin A in a manner which should be apparent to those skilled in the art. For example, in the Example 1, the intensity of the isotopic ion peak (III$_{3a}$) was obtained using an analysis software for calculating an intensity distribution thereof. Molecular Weight Calculator ver. 6.45 (http://ncrr.pnl.gov/software/) was used as the analysis software.

According to this software, the intensity of the isotopic ion peak (III$_{3a}$) was calculated as 0.2618A. Thus, the intensity B of the principal ion peak (III$_{3b}$) of the $^{18}$O-oxide is derived by subtracting 0.2618A from the intensity C of the peak (III$_{3c}$).

In the above manner, the ratio A/B of the oxidized methionine residue-containing Neurokinin A to the non-oxidized methionine residue-containing Neurokinin A in the sample [2-0] is calculated as A: (C−0.2618A).

As above, an oxidation degree of the original sample [2-0] can be obtained by acquiring mass spectra of the modified sample having the methionine residue with a stabilized oxidation state, identifying the principal ion peak (II$_{3a}$) of the $^{16}$O-oxide and the peak (III$_{3c}$), and calculating the intensity of the isotopic ion peak (III$_{3a}$) of the $^{16}$O-oxide.

What is claimed is:

1. A method of analyzing an oxidation state of a methionine residue in a protein sample, while accurately reflecting an in vivo oxidation state of the methionine residue, comprising the steps of:
   inducing a reaction between a protein sample having a methionine residue with an oxidation state to be analyzed, and hydrogen peroxide $H_2{}^{18}O_2$ having oxygen atoms labeled by the isotope $^{18}O$, to obtain a modified protein sample in which said oxidation state of said methionine residue is stabilized in order to protect from any further oxidation until it is subjected to a measurement operation; and
   subjecting said modified protein sample to a measurement to quantify an oxidation degree of said methionine residue.

2. The method as defined in claim 1, wherein said measurement is a mass spectrometric (MS) measurement using a mass spectrometer.

3. The method as defined in claim 2, which further comprises subjecting said modified protein sample to an $MS^n$ measurement (wherein n is an integer of 2 or more) to specify an oxidized site of said methionine residue.

4. A method of analyzing an oxidation state of a methionine residue in a protein sample while accurately reflecting an in vivo oxidation state of the methionine residue, comprising:

(i) inducing a reaction between a first protein sample A having a methionine residue with an oxidation state to be analyzed, and hydrogen peroxide $H_2{}^{18}O_2$ having oxygen atoms labeled by the isotope $^{18}O$, to obtain a first modified protein sample A' in which said oxidation state of said methionine residue is stabilized in order to protect from any further oxidation until it is subjected to a measurement operation, and subjecting said first modified protein sample A' to a measurement to quantify an oxidation degree of said methionine residue in said first modified protein sample A';

(ii) inducing a reaction between a second protein sample B having a methionine residue with an oxidation state to be analyzed, and hydrogen peroxide $H_2{}^{18}O_2$ having oxygen atoms labeled by the isotope $^{18}O$ to obtain a second modified protein sample B' in which said oxidation state of said methionine residue is stabilized in order to protect from any further oxidation until it is subjected to a measurement operation, and subjecting said second modified protein sample B' to a measurement to quantify an oxidation degree of said methionine residue in said second modified protein sample B'; and (iii) comparing between respective measurement results in said operation (i) and said operation (ii).

* * * * *

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: AMIDATION
```

```
<400> SEQUENCE: 1

His Lys Thr Asp Ser Phe Val Gly Leu Met
1               5                   10
```